United States Patent [19]

Meisch et al.

[11] 4,312,352
[45] Jan. 26, 1982

[54] HANGER, HOOK AND HANDLE ASSEMBLY FOR URINARY DRAINAGE BAG

[75] Inventors: Charles E. Meisch, Hasbrouck Heights; Robert N. Baker, Basking Ridge, both of N.J.

[73] Assignee: C. R. Bard, Inc., Murray Hill, N.J.

[21] Appl. No.: 116,625

[22] Filed: Jan. 29, 1980

[51] Int. Cl.³ .............................................. A61F 5/42
[52] U.S. Cl. .................................... 128/294; 128/275; 224/252
[58] Field of Search ............... 128/275, 294, DIG. 24, 128/295; 248/95, 214; 224/45, 252, 253, 269; 4/231

[56] References Cited

U.S. PATENT DOCUMENTS

| | | | |
|---|---|---|---|
| 3,088,126 | 5/1963 | Klinger | 248/214 |
| 3,090,968 | 5/1963 | Buono | 128/DIG. 24 |
| 3,220,434 | 11/1965 | Garth | 128/DIG. 24 |
| 3,345,023 | 10/1967 | Scott et al. | 128/275 |
| 3,534,738 | 10/1970 | Hook | 248/95 |
| 4,254,771 | 3/1981 | Vidal | 128/275 |

Primary Examiner—Robert W. Michell
Assistant Examiner—J. L. Kruter
Attorney, Agent, or Firm—Dennison, Mesrole, Pollack & Scheiner

[57] ABSTRACT

A unitary carrying handle-support hook assembly for urine drainage bags molded from a single plastic piece and including a pair of hanger hooks connected by a living hinge to a main frame which is provided with finger receiving apertures. The hooks can be stowed and latched in a nonuse position. The assembly includes opposed arm members receivable in pockets adjacent the top of the drainage bag.

7 Claims, 9 Drawing Figures

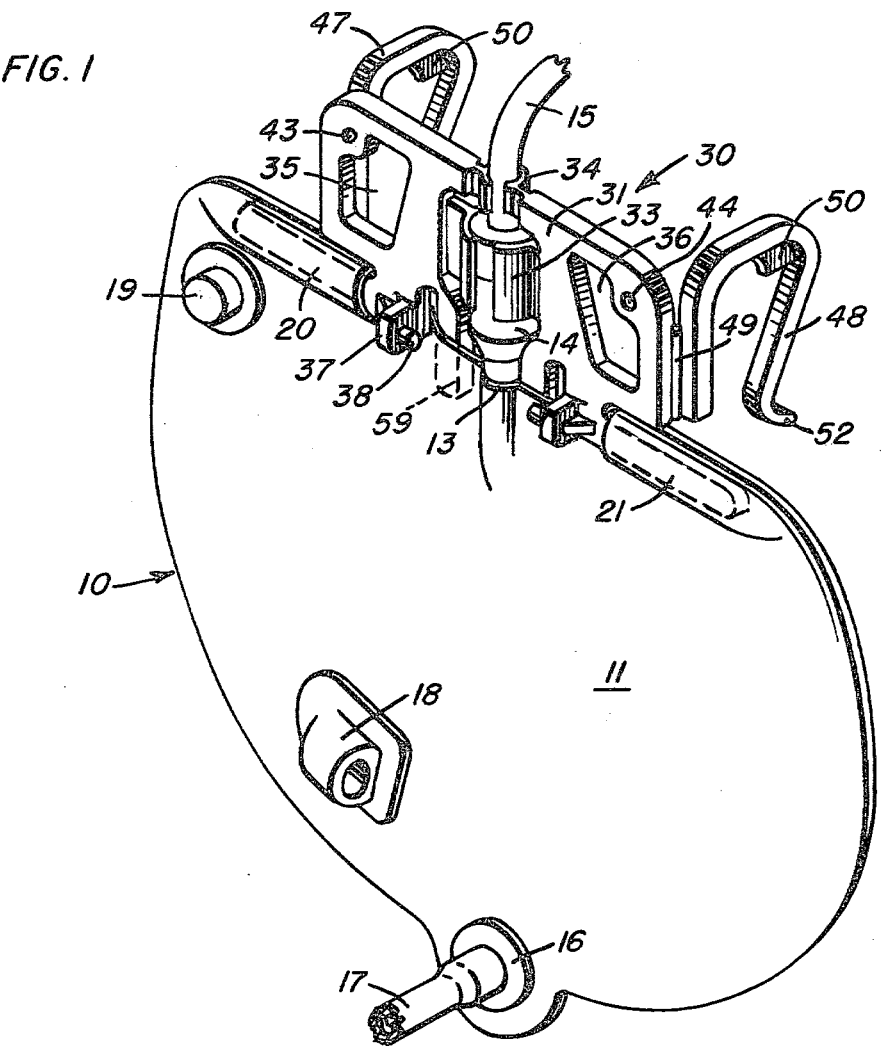
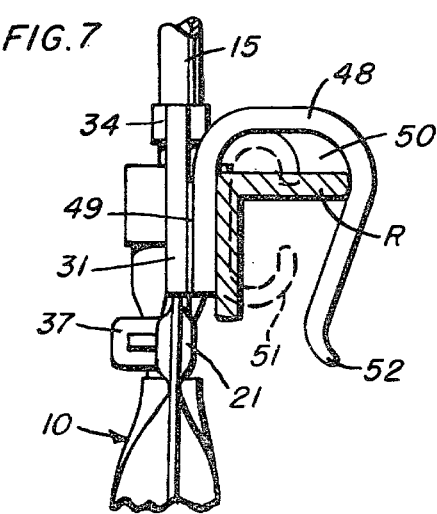
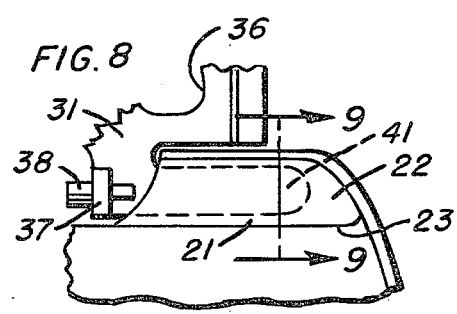
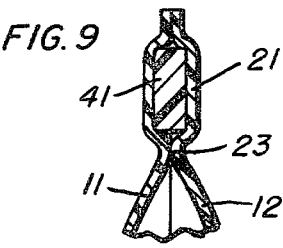

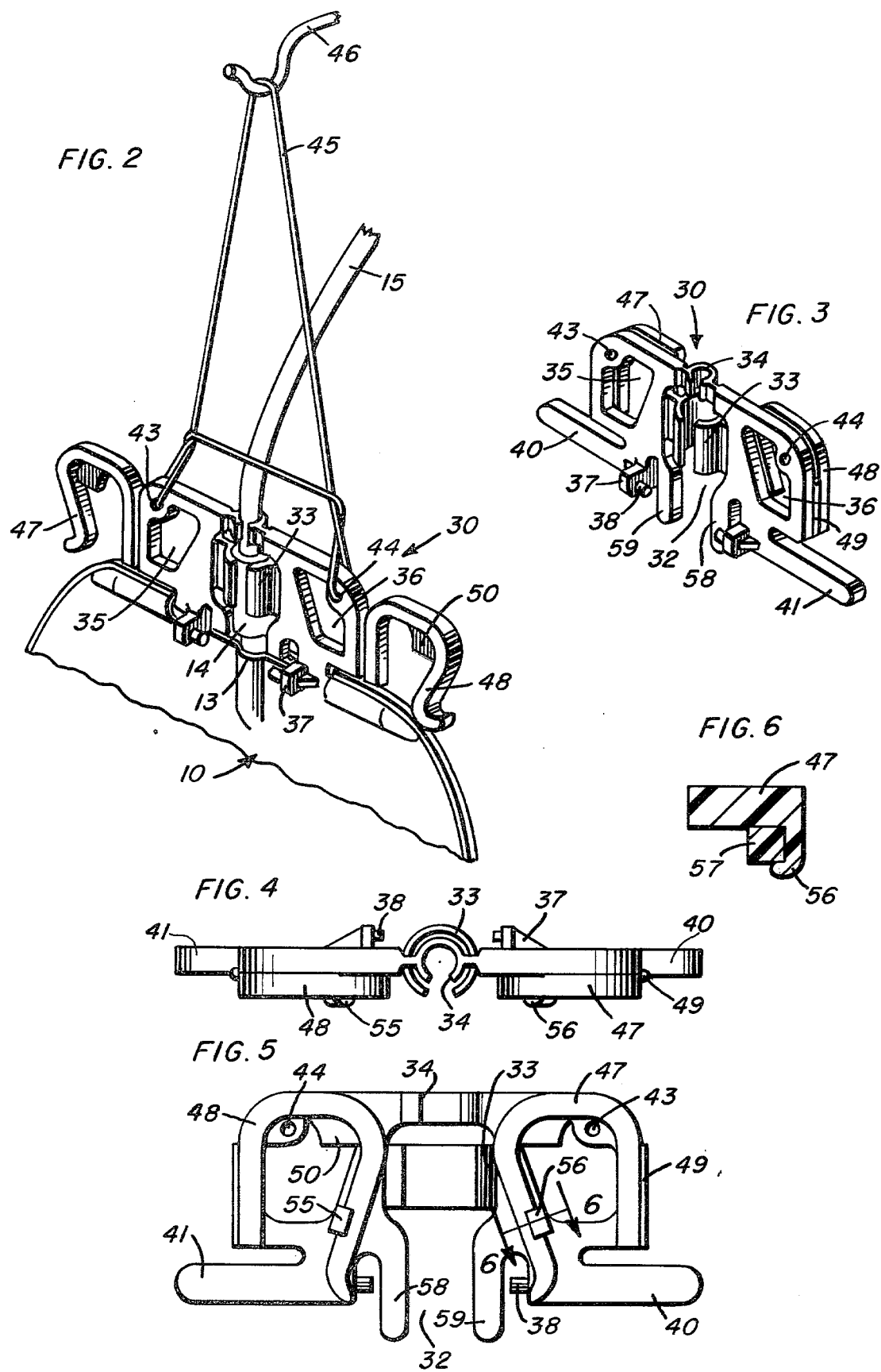

HANGER, HOOK AND HANDLE ASSEMBLY FOR URINARY DRAINAGE BAG

BACKGROUND OF THE INVENTION

The present invention relates broadly to a closed system urinary drainage bag of the type conventionally used in hospitals where it is frequently necessary to collect urine from a patient. Such bags are used routinely by post-operative patients as well as those with urological disorders. In use, the patient is catheterized, and the catheter then connected to the drainage bag through a length of tubing. The bag is supported below the patient either from the bed rail or other support, and the urine drains by gravity from the patient through the catheter, the tubing, and then into the bag. More particularly, the invention herein relates to a novel unitary hanger, hook, and carrying handle assembly for use with such urinary drainage bags.

Presently, urinary drainage bags are provided with a variety of hanger support structures. For example, Holbrook et al U.S. Pat. No. 3,776,231 disclose an integral plastic handle member and a cord adapted to be looped over a bed rail. Spurrier et al U.S. Pat. No. 3,537,109 utilize an integrally molded hanging strap which forms part of the handle assembly and which is manually torn off and then secured about a bed rail. A somewhat more complex multipiece drainage bag support bracket is shown in the Scott et al U.S. Pat. No. 3,345,023. These are the most pertinent prior art references known to applicants at present.

The principal advantages of the present invention over the known prior art are the simplicity in design and construction and the adaptability of the assembly for secure attachment to any type of support.

SUMMARY AND OBJECTS OF THE INVENTION

A multifunction, single piece hanger, hook and handle assembly is provided for simple attachment to a closed system urine drainage bag. Opposed attaching arms on the assembly fit within sealed tubular pockets on the drainage bag. The midportion of the assembly has geometrically shaped holes to receive the fingers for carrying the bag, and a clip is provided to accommodate a drip chamber as well as to support the drain tube extending into the chamber. Apertures are provided on the handle for reception of the free ends of a conventional hanging cord and a pair of hook support members is connected by a "living hinge" to the ends of the handle. Latch means are formed on the back of the handle for securing the hook support members in a nonuse position.

It is a primary object of the present invention to provide a one-piece hanger, hook and handle assembly for urinary drainage bags which may be secured to any convenient support.

It is a further object of this invention to provide a hanger-handle assembly for urinary drainage bags which is of simple one-piece construction and yet is secure, reliable and safe in use and which may be used by relatively unskilled hospital employees.

A further object is to provide a hanger-handle assembly for urinary drainage bags which may be easily and inexpensively manufactured from plastic material and which may be readily hand carried when filled without danger of spilling the bag contents.

Various other objects and advantages of our invention will be readily apparent from the following detailed description taken in conjunction with the drawings in which an exemplary embodiment of the invention is shown.

DESCRIPTION OF THE DRAWINGS

FIG. 1 is a perspective of the invention attached to a conventional urine drainage bag with the hook members in operative position.

FIG. 2 is a partial perspective similar to FIG. 1 showing use of a cord support and with the hook members fully opened.

FIG. 3 is a perspective of the hanger, hook and handle assembly alone with the hook members stowed and locked.

FIG. 4 is a top plan view of the assembly shown in FIG. 3.

FIG. 5 is a rear elevation of the assembly shown in FIG. 3.

FIG. 6 is an enlarged cross-section showing the hook clamp taken along lines 6—6 of FIG. 5.

FIG. 7 is a partial end view of the FIG. 1 assembly showing attachment to a bed rail in section and an oval rail in dotted lines.

FIG. 8 is a partial front elevation of the FIG. 1 assembly showing the manner of attachment of the assembly to a urine drainage bag.

FIG. 9 is a cross-section taken along lines 9—9 of FIG. 8.

DESCRIPTION OF A PREFERRED EMBODIMENT

Referring now to the drawings, a conventional closed system urine drainage bag is shown generally at 10 and is formed by peripherally heat sealing or otherwise securing a pair of flat vinyl or PVC sheets 11 and 12. The bag is provided with an inlet opening 13 on its top edge for reception of a drip chamber 14 and its associated tubing 15 which connects to a catheter which is in turn inserted in the urethral canal of the patient.

The bag 10 also includes a drain 16 terminating in a latex conduit 17 which when not in use may be clamped off in a well known manner and the free end received in housing 18 which is sealed to face 11 of the bag. An air vent and bacteria filter are also fitted at 19 in the conventional manner.

As best shown in FIGS. 1, 8 and 9, the top of bag 10 on either side of opening 13 is formed with heat sealed pockets 20 and 21 open toward the center and closed at their extremities. In the preferred form the sheets 11 and 12 are initially formed with extensions or tabs 22 as seen in FIG. 8 which are heat sealed as at 23 to form the pockets. The pockets 20 and 21 are adapted to receive the opposed arms of the handle-hanger assembly as described further herein.

The hanger-handle assembly which represents the present invention is shown generally at 30 and is molded in a single piece from polypropylene, polyethylene or any other suitable plastic material. This assembly includes a central main frame 31 which has a cut-out 32 at its center in which is formed a resilient drip chamber receiving clip 33. Immediately above cut-out 32 a circular split tubing collar 34 is provided to receive inlet tube 15. A finger receiving cut-out 35, 36 is formed on either side of the central cut-out 32 to facilitate carrying of a filled bag.

Optional bosses 37 each with an inwardly turned trunnion pin 38 are located on one side of main frame 31 and at its lower edge for use in pivotally supporting a plastic meter which may be used in conjunction with some bags but which is not used in the bag depicted herein.

Oppositely directed bag support arms 40, 41 extend outwardly away from the bosses 37 and are adapted for reception in the bag heat sealed pockets 20 and 21 as previously described. (See FIGS. 8 and 9). It will be understood that the vinyl material of the bag is quite flexible so that the arms may be easily inserted in the pockets without undue risk of bag tearing during assembly.

For those situations when it is desired to use a cord suspension for the bag, a pair of eyelets 43, 44 are formed on the top part of the main frame 31. A cord 45 may be passed through these eyelets and tied so that the entire assembly may be suspended from a hook 46 as shown in FIG. 2.

A pair of hook shaped hanger members 47 and 48 are made integral with the main frame 31 through a thin living hinge 49 on the rear edge so that the hanger members can pivot rearwardly from the FIG. 2 position (fully extended) through the use position of FIG. 1 (90° rotation) to the stowage position of FIG. 3 (180° rotation). The term "living hinge" is used herein to designate a well-known type of hinge used in plastic manufacture wherein two members are integrally and hingedly interconnected by a thin bendable web.

Each hanger member has formed on the inside upper corner thereof an anti-tip spacer 50 which rests on top of the support such as bedside rail R and prevents excessive bag tilt due to shifting of the center of gravity as the bag fills. The configuration of the hook shaped hanger is such that it will readily fit over round or oval side rails as well as shown in dotted outline at 51 in FIG. 7. The free end of the hook shaped hanger is beveled outwardly at 52 and the inherent resiliency of the member permits it to be attached when pivoted to the FIG. 1 use position over any available horizontal support.

In order to secure the hanger members in an out-of-the-way stowage position as in FIGS. 3 and 4, integral latch members 55, 56 extend rearwardly from the main frame 31 and the free arm 57 of the hanger member may snap into locked engagement behind the latch as shown in FIG. 6. It will be noted that in the folded and stowed position, the central open portions of the hanger members overlie the finger receiving cut-outs 35 and 36 and therefore present no obstacle to the carrying handle function. See FIGS. 3 and 5.

In order to provide additional strength to the assembly, especially when a bag with a volume meter is used, a pair of depending back supports 58 and 59 extend downwardly from the main frame and the bag rests thereagainst.

Drainage bags and handle-hanger assemblies of the type disclosed herein are designed for but a single use by a patient in order to prevent cross-contamination and to obviate the need for expensive and time consuming sterilization. The injection molded unitary hanger, hook, and handle assembly of our invention provides an inexpensive multi-function means for using such urine drainage bags.

We claim:

1. In combination with a urine drainage bag having an inlet adapted for connection to a urinary catheter, and a support for said bag, the improvement comprising the support for the bag including an elongated main frame member having opposed ends, means for attaching said main frame member to the top of said bag, finger receiving apertures in said main frame member to facilitate carrying said bag and a hook-shaped hanger member hingedly connected to each end of said main frame member and movable to either a stowed position overlying said main frame member, or to a use position at substantially right angles to said main frame member, wherein said main frame member and hanger members are formed of a single piece of plastic material, each said hanger member being integrally connected to the main frame members by an integral living hinge.

2. A urine drainage bag and support as defined in claim 1 and further including eyelets in said main frame member on either side of the center thereof, and a cord support looped through said eyelets.

3. A urine drainage bag and support as defined in claim 1, and further including integral latch means on one face of said main frame member for securing the hanger members in the stowed position.

4. A urine drainage bag and support as defined in claim 1, and further including anti-tip spacer means fixed on the inner edge and within each hook-shaped hanger cooperable with a support rail to resist rotation and tipping of the bag and the main frame member about said support rail and the longitudinal axis of said main frame member.

5. In combination with a urine drainage bag having an inlet adapted for connection to a urinary catheter, elongated pockets adjacent the top of said bag and a support for said bag, the improvement comprising the support for the bag including an elongated main frame member having opposed ends, a pair of bag attachment arms on the bottom of said main frame member received in said elongated pockets for securing the main frame member to said bag, finger receiving apertures in said main frame member to facilitate carrying said bag, and a hook-shaped hanger member hingedly connected to each end of said main frame member and movable to either a stowed position overlying said main frame member, or to a use position at substantially right angles to said main frame member, and wherein said main frame member and hanger members are formed of a single piece of plastic material, each said hanger member being integrally connected to the main frame members by an integral living hinge.

6. A urine drainage bag and support as defined in claim 1, and further including a pair of legs depending from one side of said main frame, said legs supporting the side of said bag.

7. A unitary handle and support assembly for a urine drainage bag comprising, an elongated main frame member having opposed ends, means on the lower portion of said main frame member for securing said assembly to the top of said bag, finger receiving apertures in said main frame member shaped to receive the fingers to facilitate carrying said bag, and a hook-shaped hanger member hingedly connected to each end of said main frame member and movable to either a stowed position overlying said main frame member, or to a use position at substantially right angles to said main frame member, wherein said main frame member and hanger members are formed of a single piece of plastic material, each said hanger member being integrally connected to the main frame members by an integral living hinge.

* * * * *